United States Patent [19]

Bonello et al.

[11] Patent Number: 4,787,399
[45] Date of Patent: Nov. 29, 1988

[54] REMOTE CONTROLLED CATHETER GUIDE

[75] Inventors: Philippe Bonello, Geneva; Maurice Jeanmonod, Meyrin, both of Switzerland

[73] Assignee: Sarcem S.A., Meyrin, Switzerland

[21] Appl. No.: 69,532

[22] Filed: Jul. 1, 1987

[30] Foreign Application Priority Data

Jul. 29, 1986 [CH] Switzerland ............... 3146/86

[51] Int. Cl.$^4$ .................................. A61B 5/00
[52] U.S. Cl. ..................... 128/772; 604/95; 604/96; 128/657
[58] Field of Search ........... 128/657, 772, 344, 348.1; 604/95, 96, 103, 164, 171, 264, 280, 282

[56] References Cited

U.S. PATENT DOCUMENTS

| | | | |
|---|---|---|---|
| 3,416,531 | 12/1968 | Edwards | 128/772 |
| 3,521,620 | 7/1970 | Cook | 128/772 |
| 3,528,406 | 9/1970 | Jeckel et al. | 128/772 |
| 3,757,768 | 9/1973 | Kline | 604/95 |
| 3,841,308 | 10/1974 | Tate | 128/772 |
| 3,847,140 | 11/1974 | Agella | 128/772 |
| 3,854,473 | 12/1974 | Matsuo | 128/772 |
| 4,119,099 | 10/1978 | Patel | 604/103 |
| 4,150,676 | 4/1979 | Jackson | 128/351 |
| 4,215,703 | 8/1980 | Willson | 128/772 |
| 4,456,017 | 1/1984 | Miles | 128/772 |
| 4,616,653 | 10/1986 | Samson et al. | 604/95 |
| 4,676,249 | 1/1987 | Arenas et al. | 604/164 |

FOREIGN PATENT DOCUMENTS 2130885 6/1984 United Kingdom.

*Primary Examiner*—Max Hindenburg
*Attorney, Agent, or Firm*—Young & Thompson

[57] ABSTRACT

The invention relates to a remote controlled catheter guide provided with a micro-balloon which comprises a head formed of a coil spring (4) mounted at the end (2) of a tube (1). When pulling on a flexible traction member (7) fastened to an eccentric point inside the end of the head, this head can be curved at will. The remote controlled catheter guide with micro-balloon is thus constituted of the assembly of elements forming a channel through which it is possible to locate the flexible traction (8) which is inflatable through its feeding duct (9) it is possible to carry out the pre-dilatation of stenosis so that afterwords a conventional catheter can be slid in place over the catheter-guide.

6 Claims, 1 Drawing Sheet

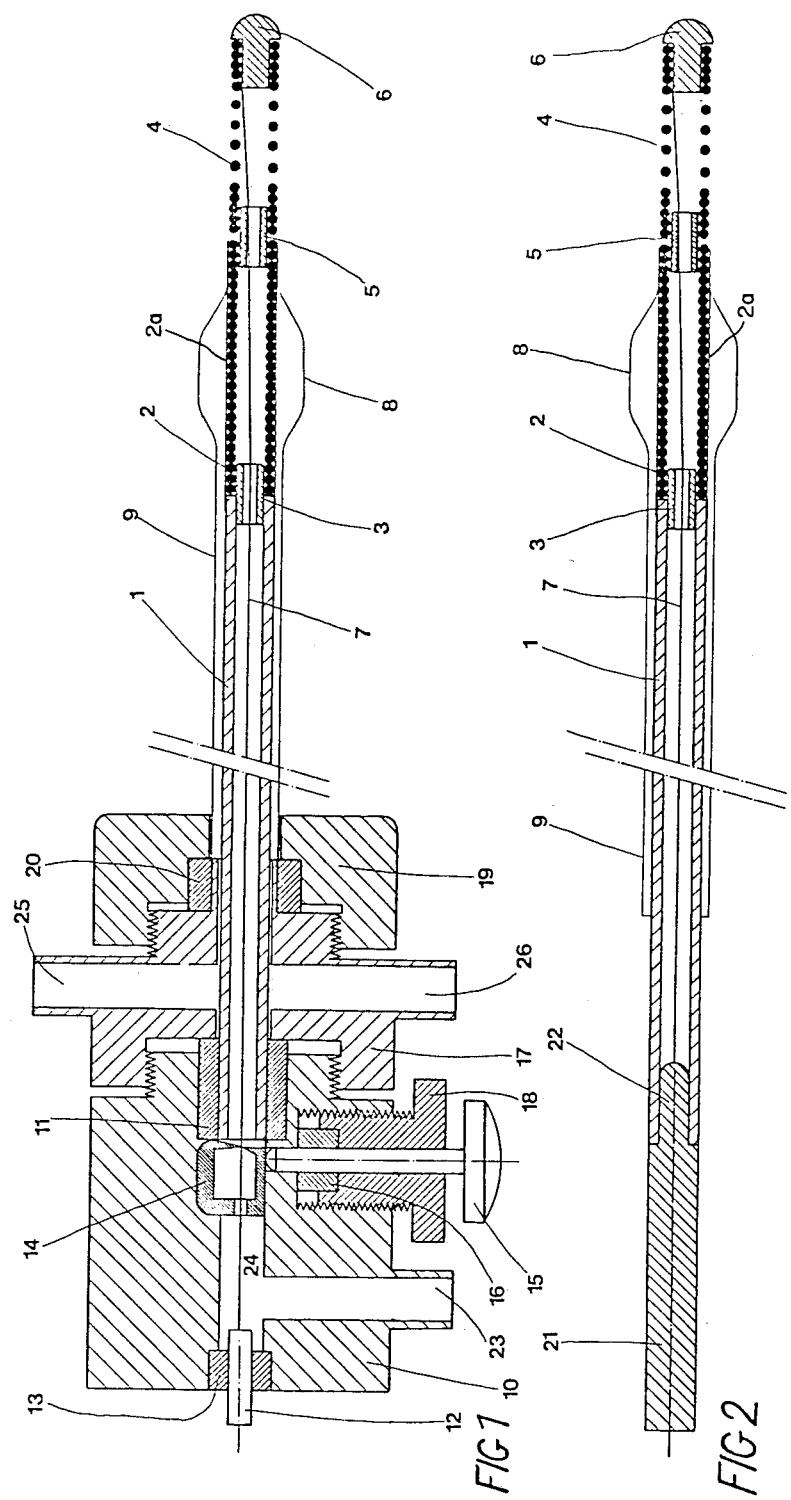

REMOTE CONTROLLED CATHETER GUIDE

FIELD OF THE INVENTION

The present invention relates to a remote controlled catheter guide provided with a micro-balloon which is to be mainly used in the treatment of cardio-vascular deseases, particularly of the coronary vessels.

The treatment of the narrowing of an arteria or stenosis is currently done through dilatation of the balloon of an instrument called a catheter. It is not always simple or even possible to place the said inflatable balloon inside the stenosis due to the multiple ramifications of the blood vessels and when the narrowing of the vessel is too great.

Nowadays, to be able to put in the right place the inflatable balloon of the catheter one first introduces in the blood vessels and into the stenosis a very thin metallic rod having a curved end. This rod is then used as a guide for a catheter with an inflatable balloon which is slid over said rod up to the locations of the narrowings.

This method is currently used but has the drawback of using a guide having a fixed curvature at its end which cannot be modidied as a function of the variable successive directions it has to take through the multiple ramifications of blood vessels. It is further impossible to inject through said guide a contrast liquid to control its positioning.

The present invention relates to a polyvalent guide for a catheter obviating the precited drawbacks but which has the further advantage of being provided with a micro-balloon for obtaining the pre-dilatation of very strong stenosis where the remaining passage for the blood has got so narrow that the normal catheter balloon cannot be used.

In fact the micro-balloon is intended to work within diameters to 0.6 to 2 millimeters for a full expansion with regard to the commonly used balloons the expansion of which starts only at a diameter of about 2 millimeters.

When the aperture of the stenosis has been first widened by mean of the micro-balloon of the guide it is then possible to slide in place over said guide a catheter with a normal balloon up to all narrowing zones in order to further expand the stenosis through subsequent dilatation.

DESCRIPTION OF THE DRAWINGS

FIG. 1 shows schematically one embodiment of the catheter-guide provided with its remote control for its setting in place.

FIG. 2 shows the catheter-guide after having been set in place and ready to be used as a guide for a conventional catheter.

DESCRIPTION OF THE PREFERRED EMBODIMENT

The remote controlled catheter-guide provided with a micro-balloon comprises a tube (1) the extremity 2 of which is formed of a cylindrical coil spring the coils of which are abutting and covered by a plastic coating 2a. The end of said coil spring is fitted on a sleeve 3 itself fitted into the tube 1. The head of the catheter-guide is formed of coil spring 4 having spaced coils, at least in its central position, fitted on a sleeve 5 itself fitted into the free end 2 of the tube 1. A cap 6 is fitted in the free end of the spring 4. A flexible traction member 7 is fixed to the cap 6 in an eccentric location and extends throughout the head and the tube to enter a control member. A metallic rod can be provided within the tube 1 to increase its rigidity, this rod is not shown. An inflatable micro-balloon 8 is located around the extremity 2 of the tube and connected to a feeding tube 9.

A control unit 10 is fixed to the other end of the tube 1 in a removable manner and tightly by means of an a sealing ring 11. This unit 10 comprises a cylindrical part 12 fixed to the flexible traction member 7 and sliding tightly, due to sealing ring 13, in said unit 10. Said control unit comprises further a cutter 14 and its operating member 15 sliding fluid tightly in the unit 10 by mean of an a sealing ring 16 and a threaded member 18. The control unit comprises further first 17 and second 19 threaded elements fluid tightly assembled with the unit 10 respectively with the first element 17 by mean of sealing rings 11 and 20.

First of all, before any surgical intervention, one makes sure that the three threaded elements 17, 18 and 19 are fully screwed to secure fluid tightly the control unit 10 with the tube 1, the push member 15 and the feeding circuit for the micro-balloon respectively. In order to set in place the catheter-guide in one or the other circulatory ramifications up to the inside of the area to be treated the user has therefore three degrees of movement; to go back and forth with the whole assembly, to rotate the whole assembly on itself in one direction or the other and to curve or bend the head or to let it straighten again. The said latter function is obtained by pulling the flexible traction member 7, through part 12, bending the coil spring 4. When the traction is released on member 7 the coil spring straighten due to its elasticity. The displacement of member 12 with respect to the control unit 10 can be obtained manually or by a non-illustrated mechanism for example of the micrometric type.

A contrast liquid can be introduced into the blood vessel in question to locate by means of a radiological examination the head of the catheter guide. The liquid is injected in channel 23 of the control unit 10, fills the chamber 24 and the tube 1 as well as its extremity 2 and is let out into the blood vessel between the spaced coils of the spring 4.

Finally to inflate the micro-balloon 8, a pressurized fluid is fed through the channel 25 into the feeding duct 9 and the balloon 8. The channel 26 is provided in case said fluid being a liquid it would be necessary to evacuate the air contained in the duct 9 and the balloon 8.

When the catheter-guide is in place and after having pre-expanded the stenosis or the several stenoses with the inflation of the micro-balloon 8, the user unscrews the threaded element 18 to liberate the push member 15. He then pushes said member 15 actuating the cutter 14 to cut the flexible traction member 7. Thereafter the screwed elements 17 and 19 are unscrewed totally liberating the feeding duct 9 and the tube 1 which can then be withdrawn from the control unit 10.

Finally it is possible to replace the control unit 10 by a handle 21 one end of which is fitted into the end of tube 1, as shown in FIG. 2.

Then a normal catheter is slid over the handle 21 and the tube 1, which are then used as a conventional catheter-guide.

We claim:

1. In a remote controlled catheter-guide comprising a thin and flexible tube, one end of which is fixed to a head and the other end of which is removably fixed to a control unit, said head comprising a coil spring secured at one end to said flexible tube and closed at its other end, said spring having spaced coils at least in its central zone, and an operating member sliding in the control unit and connected to an eccentric point of said closed end of said head by a flexible traction member; the improvement in which the end of the tube that carries the head is comprised by a coil spring having abutting coils covered by a fluid-tight casing, an inflatable microballoon surrounding said casing, and a duct connecting said microballoon to a channel in the control unit for the introduction of a fluid into the microballoon to inflate the microballoon.

2. Catheter-guide according to claim 1, in which the extremity of the coil spring with abutting coils is fitted on a sleeve, this latter being partly driven into a portion of the tube which is disposed between said coil spring with abutting coils and said control unit.

3. Catheter-guide according to claim 1, in which the coil spring of the head is fitted on a sleeve, said latter being partly driven into the adjacent end of the tube.

4. Catheter-guide according to claim 1, in which the control unit has a cutter intended to cut the flexible traction member.

5. Catheter-guide according to claim 1, in which the channel is formed by an envelope concentric to the tube, the channel having one end integral with the micro-balloon.

6. Catheter-guide according to claim 5, in which the other end of the envelope is fluid tightly mounted on the control unit whereas the end of the microballoon remote from the channel is fluid tightly mounted on the fluid-tight casing of the coil spring forming the extremity of the tube.

* * * * *